United States Patent [19]
Lecomte et al.

[11] Patent Number: 5,910,617
[45] Date of Patent: Jun. 8, 1999

[54] PROCESS FOR THE PREPARATION OF ALIPHATIC OR CYCLOALIPHATIC CHLORIDES

[75] Inventors: Loic Lecomte; Serge Metge; Denis Souyri, all of Toulouse, France

[73] Assignee: Societe Nationale Des Poudres Et Exploisfs, Paris Cedex, France

[21] Appl. No.: 09/099,491

[22] Filed: Jun. 18, 1998

[30] Foreign Application Priority Data

Jul. 16, 1997 [FR] France ................................. 97 09031

[51] Int. Cl.⁶ ..................... C07C 17/16; C07C 22/00; C07C 43/18; C07C 255/00
[52] U.S. Cl. ................. 570/261; 570/198; 570/258; 568/610; 568/614; 568/655; 568/681; 558/425; 558/460
[58] Field of Search ..................... 570/198, 258, 570/261; 568/610, 614, 655, 681; 558/425, 460

[56] References Cited

U.S. PATENT DOCUMENTS

| | | |
|---|---|---|
| 2,926,204 | 2/1960 | Wolfe . |
| 4,734,535 | 3/1988 | Greif et al. . |
| 4,806,286 | 2/1989 | Senet et al. . |
| 5,196,611 | 3/1993 | Henkelmann et al. . |
| 5,348,923 | 9/1994 | Gauthier et al. . |

FOREIGN PATENT DOCUMENTS

| | | |
|---|---|---|
| 0645357 | 3/1995 | European Pat. Off. . |

*Primary Examiner*—Alen Siegel
*Attorney, Agent, or Firm*—Bucknan and Archer

[57] ABSTRACT

The process according to the invention consists in preparing chlorides of aliphatic or cycloaliphatic hydrocarbons by reacting the corresponding mono- or polyalcohol with phosgene or thionyl chloride in the presence of at least one catalyst chosen from hexasubstituted guanidinium halides and their hydrohalides, optionally grafted via one of their radicals to a silica-based support.

The chlorides are quickly obtained with good yields and contain few by-products such as carbonates or chloroformates.

12 Claims, No Drawings

PROCESS FOR THE PREPARATION OF ALIPHATIC OR CYCLOALIPHATIC CHLORIDES

The present invention relates to a novel process for the preparation of chlorides of aliphatic or cycloaliphatic hydrocarbons by reaction of the corresponding alcohol with phosgene or thionyl chloride in the presence of a hexasubstituted guanidinium salt as catalyst.

Chlorides of aliphatic or cycloaliphatic hydrocarbons are known compounds which are widely used as such or as organic synthetic intermediates, in particular in the field of polymers or in that of plant protection.

Aliphatic chlorides can be prepared from the corresponding alcohol by reacting them with hydrochloric acid but the reaction is reversible and the conversion is incomplete. Its implementation is lengthy and difficult. It is often necessary to operate under a pressure greater than atmospheric pressure. Isomeric compounds and other by-products are formed, as well as a troublesome aqueous phase. Furthermore, this process does not allow the appropriate conversion of alcohols containing functional groups which are highly sensitive to hydrochloric acid and in particular unsaturated alcohols.

A number of processes in which an alcohol is reacted with phosgene in the presence of a catalyst have been disclosed.

In Patent Application EP 645,357, the reaction of the alcohol with phosgene is carried out in the presence of catalysts which are addition compounds of N,N-disubstituted formamides with phosgene but these formamide derivatives degrade at high temperature and give rise to numerous by-products.

According to the process of Patent Application EP 514,683, the alcohol is reacted with phosgene or thionyl chloride in the presence of phosphine oxides as catalysts. The reaction is very long and phosphorus-comprising impurities are formed.

According to other processes, the chloroformates are first of all formed and subsequently decomposed in the presence of catalysts, such as quaternary phosphonium or ammonium salts as disclosed in U.S. Pat. No. 4,734,535. However, some chloroformates, such as, for example, propargyl chloroformate, are very difficult to prepare. Furthermore, chloroformates are highly reactive with respect to alcohols which are used to prepare them. Large amounts of by-products, such as carbonates, are formed. It is subsequently necessary to separate them. Some of these carbonates are dangerous at the reaction temperatures used. The quaternary ammoniums used as catalysts lose their activity during the reaction and cannot be reused.

The subject-matter of the invention is a process for the preparation of chlorides of aliphatic or cycloaliphatic hydrocarbons, from the corresponding alcohols, which does not exhibit the abovementioned disadvantages.

According to the process of the invention, chlorides of substituted or unsubstituted, saturated or unsaturated, aliphatic or cycloaliphatic hydrocarbons are prepared by reaction of the corresponding mono- or polyalcohol with phosgene or thionyl chloride in the presence of at least one catalyst chosen from the group consisting of -(1) hexasubstituted guanidinium halides and their hydrohalides, of formula II:

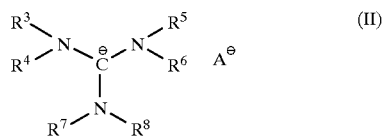

in which the $R^3$ to $R^8$ radicals, which are identical or different, represent substituted or unsubstituted, linear or branched, $C_1$ to $C_{12}$ alkyl groups and/or substituted or unsubstituted, $C_5$ to $C_6$ cycloalkyl groups and A represents a chlorine or bromine atom or an $HCl_2$ or $HBr_2$ group, and -(2) hexasubstituted guanidinium halides and their hydrohalides, grafted via one of their radicals to a silica-based support, of formula (III):

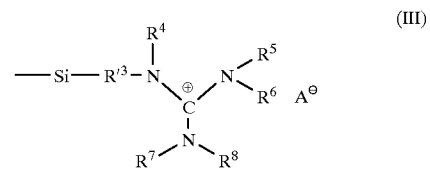

in which the $R^4$ to $R^8$ radicals and the anion A have the above meanings and the $R'^3$ radical represents a $C_2$ to $C_{10}$ alkylene group.

The alcohols used as starting materials are preferably mono- or polyalcohols of formula (I):

in which $R^1$ and $R^2$, which are identical or different, represent a hydrogen atom, a saturated or unsaturated, substituted or unsubstituted, linear or branched, $C_1$ to $C_{30}$, preferably $C_1$ to $C_{22}$, aliphatic group, a saturated or unsaturated, substituted or unsubstituted, $C_3$ to $C_{12}$, preferably $C_3$ to $C_8$, cycloaliphatic group, a saturated or unsaturated, substituted or unsubstituted, $C_1$ to $C_{30}$ alkoxy group, or a substituted or unsubstituted aryl or aryloxy group;

or else in which $R^1$ and $R^2$ together form, with the carbon to which they are attached, a saturated or unsaturated, substituted or unsubstituted, $C_3$ to $C_{12}$ cycloaliphatic group.

The substituents of $R^1$ and $R^2$ can be chosen from halogen atoms, in particular fluorine, chlorine and bromine atoms, hydroxyl groups, saturated or unsaturated, substituted or unsubstituted aliphatic groups, haloaliphatic groups, in particular the trifluoromethyl group, saturated or unsaturated, substituted or unsubstituted cycloaliphatic groups, substituted or unsubstituted aryl groups, saturated or unsaturated, substituted or unsubstituted araliphatic groups, alkoxy groups, polyalkoxy groups, alkoxyaryl groups, aryloxy groups, nitro groups and cyano groups. These substituents, when they are hydrocarbon-comprising groups, can themselves be substituted by these various substituents.

The unsaturated bonds of the aliphatic chains comprised within $R^1$ and $R^2$ can be double and/or triple bonds.

The preferred alcohols are the alcohols in which $R^1$ and $R^2$, which are identical or different, represent a hydrogen atom or a following substituted or unsubstituted group:

$C_1$ to $C_{22}$, particularly $C_1$ to $C_8$, alkyl;

$C_2$ to $C_{22}$, particularly $C_2$ to $C_8$, alkenyl, such as vinyl or allyl;

$C_2$ to $C_{22}$, particularly $C_2$ to $C_8$, alkynyl and in particular ethynyl;

$C_1$ to $C_{22}$, particularly $C_1$ to $C_4$, alkoxy, such as ethyloxy or propoxy;

aryl, such as phenyl and naphthyl;

aryloxy, in particular phenoxy;

$C_1$ to $C_{22}$ hydroxyalkyl or polyhydroxyalkyl;

$C_2$ to $C_{22}$ hydroxyalkenyl or hydroxylalkynyl;

$C_2$ to $C_{22}$ polyhydroxyalkenyl or polyhydroxy- alkynyl;

$C_3$ to $C_{12}$, particularly $C_3$ to $C_8$, cycloalkyl; or the alcohols in which $R^1$ and $R^2$ together form, with the carbon to which they are attached, a $C_3$ to $C_8$ cycloalkyl or cycloalkenyl group.

The substituents of these groups are preferably chosen from halogen atoms, in particular fluorine, chlorine and bromine atoms, $C_1$ to $C_4$ alkyl groups, $C_1$ to $C_4$ haloalkyl groups, in particular $CF_3$, $C_3$ to $C_8$ cycloalkyl groups, $C_1$ to $C_4$ alkoxy groups, $C_7$ to $C_{12}$ aralkyl groups, aryl groups, in particular the phenyl group, $C_1$–$C_{22}$ alkoxyphenyl groups, in particular the 4-methoxyphenyl group, or aryloxy groups, in particular the phenyloxy group.

Mention may be made, as examples of alcohols, of 1-butanol, 1-hexanol, 1-octanol, 1-dodecanol, 1-hexadecanol, docosanol, 1,4-butanediol, 2-butyne-1,4-diol, 1,6-hexanediol, 1,8-octanediol, 8-chloro-1-octanol, cyclohexylmethanol, 2-ethyl-1-hexanol, but-3-en-1-ol, propargyl alcohol, 2-(4-methoxyphenyl)-1-ethanol or cyclohexanol.

The process according to the invention is particularly advantageous for the preparation of chlorides of acetylenic alcohols and in particular propargyl chloride.

Thionyl chloride or, preferably, phosgene is reacted with the alcohol in a proportion of between approximately 1 and approximately 10 mol, preferably between approximately 1 and approximately 2 mol, per mole of hydroxyl group to be converted.

The reaction is generally carried out at a temperature of between approximately 20° and approximately 150° C., preferably between approximately 50° and approximately 130° C., and at atmospheric pressure. It is also possible, if necessary, to carry out the reaction under a lower or higher pressure, in particular of between approximately 0.1 bar and approximately 20 bar.

A solvent which is inert with respect to compounds and with a boiling point greater than the reaction temperature can be used in order in particular to allow better dissolution of the catalyst or to allow the catalyst to pass better into suspension and to allow better contact with the reagents.

Mention may be made, as examples of solvent, of chlorinated or non-chlorinated aromatic hydrocarbons, such as toluene, monochlorobenzene, xylenes or dichlorobenzenes, and aliphatic hydrocarbons.

The catalysts necessary for carrying out the process according to the invention are hexasubstituted guanidinium salts of formulae (II) or (III). In these formulae, A preferably represents chlorine or the $HCl_2$ group.

The substituents of the $R^3$ to $R^8$ radicals are chosen from groups which are inert under the reaction conditions, such as halogen atoms or alkyl, alkoxy, aryloxy and nitro groups.

The $R^3$ to $R^8$ radicals, which are identical or different, are preferably $C_1$ to $C_4$ alkyl groups. The $R'^3$ radical is preferably the —$(CH_2)_3$— group.

The silica supports are generally silica beads which contain silanol functional groups at the surface.

These grafted or non-grafted guanidinium salts are commercially available or can be prepared in a known way, in particular as disclosed in Patent EP 545,774.

Mention may be made, as examples of catalysts of formula (II), of hexamethylguanidinium chloride or bromide, hexaethylguanidinium chloride or bromide, hexabutylguanidinium chloride or bromide, and their hydrochlorides or hydrobromides.

Hexabutylguanidinium chloride or its hydrochloride are the preferred catalysts.

Preference is given, among catalysts of formula (III) grafted onto a silica-based support, to the catalyst in which the $R^4$ to $R^8$ radicals are butyl groups and $R'^3$ represents the —$(CH_2)_3$— group.

The amount of catalyst employed is generally between approximately 0.001 and approximately 0.20 mol of guanidinium group per mole of hydroxyl group to be converted and preferably between approximately 0.005 and approximately 0.05 mol.

The catalysts are very stable under the reaction conditions. They do not lose their activity and can easily be reused in other operations.

The process can be carried out continuously or batchwise.

When the process is carried out batchwise, it is preferable to add phosgene gradually to the reaction mixture which contains the alcohol and the catalyst and optionally a solvent.

For the preparation of some chlorides, in particular for the preparation of acetylenic chlorides, it is preferable to carry out the reaction continuously.

Thus, when the reaction is carried out starting with propargyl alcohol, the latter, which is liquid, and phosgene, which is preferably gaseous, are introduced into the reaction mixture, containing the catalyst and optionally the solvent, which has been heated to the chosen temperature, preferably of between approximately 90° C. and approximately 130° C. Propargyl chloride is quickly formed. The latter and the other gases which are given off are separated from the reaction mixture as they are formed, for example by passing them into a distillation column. Propargyl chloride is then collected. Analyses of the distillate, carried out by gas chromatography, show that it contains virtually no propargyl carbonate or chloroformate.

The process according to the invention makes it possible quickly to obtain aliphatic or cycloaliphatic chlorides with good yields and few by-products and in particular few or no chloroformates and carbonates. For the preparation of propargyl chloride, the absence of dipropargyl carbonate is particularly advantageous because the latter, because of its instability and its toxicity, is an altogether undesirable by-product.

The following examples illustrate the invention without, however, limiting it.

EXAMPLE 1

300 g of xylene (mixture of isomers), 25 g (approximately 0.058 mol) of hexabutylguanidinium chloride and 17 g (approximately 0.17 mol) of phosgene are introduced, as vessel heel, into a 1 litre round-bottomed flask equipped with a Vigreux column surmounted by a cooling system at 0° C.

The mixture is brought to 100° C. Propargyl alcohol, introduced in the liquid form using a peristaltic pump, and phosgene, introduced in the gaseous form using a dip tube, are then run in simultaneously.

The amounts introduced over 2 hours are respectively 163 g (approximately 2.9 mol) of alcohol per 398 g (approximately 4.02 mol) of phosgene. The reaction mixture is maintained at 100° C.

After the beginning of the operation in which the alcohol and phosgene are run in simultaneously, a rise in the temperature at the top of the distillation column is quickly observed. It stabilizes at approximately 60–65° C.

The amount of distillate collected is 237.5 g. Its composition, determined by gas chromatography (GC), is as follows:

Propargyl chloride: 57.6%.

Xylenes: 36.6%.

Propargyl alcohol: 2.6%.

Neither the presence of dipropargyl carbonate nor that of propargyl chloroformate is detected.

Propargyl chloride is isolated by distillation at atmospheric pressure at 60° C. The yield is 60%.

COMPARATIVE EXAMPLE 1

The same procedure is used as in Example 1 but, instead of hexabutylguanidinium chloride, 0.058 mol of dimethylformamide is introduced as vessel heel.

The operation in which the alcohol and phosgene are run in simultaneously lasts two hours, during which 400 g of phosgene and 194 g of propargyl alcohol are introduced.

250 g of distillate are collected, the composition of which, determined by GC, is as follows:

Propargyl chloride 32%

Propargyl alcohol 2.5%

Xylenes 54%

Propargyl chloroformate 11%

This example shows that, with a different catalyst from those of the invention, a markedly lower amount of propargyl chloride is obtained and a significant amount of propargyl chloroformate is obtained as by-product.

EXAMPLE 2

30 kg of xylenes and 2.5 kg of hexabutylguanidinium chloride hydrochloride are introduced, as vessel heel, into a 100 l reactor equipped with a distillation column surmounted by a cooling system and then 100 g of phosgene are added.

The mixture is brought to 100° C. Propargyl alcohol and phosgene are then run in simultaneously. The alcohol is introduced using a metering pump at a flow rate varying from 1.5 to 3 kg/h and the phosgene is introduced in the gaseous form, using a dip tube, at a flow rate varying from 3 to 7 kg/h, so that phosgene is always in excess in the reaction mixture. The temperature of the reaction mixture is maintained between 98° C. and 108° C.

74.4 kg of phosgene and 29.2 kg of propargyl alcohol are thus introduced over 15 hours.

31.9 kg of distillate are collected, this distillate being composed essentially of propargyl chloride containing 4% of residual phosgene and 3% of other impurities (determined by GC analysis). The crude yield is 80%.

EXAMPLE 3

60 g of xylene and 5 g of hexabutylguanidinium chloride hydrochloride (1 mol % with respect to the butanol) are introduced, as vessel heel, into a 250 ml three-necked round-bottomed flask equipped with a distillation column surmounted by a cooling system.

The mixture is brought to a temperature of between 120 and 130° C. Approximately 5 g of phosgene are then introduced. n-Butanol and phosgene are then run in simultaneously, so that phosgene is always in excess in the mixture. Approximately 80 g of n-butanol and 155 g of phosgene (40% excess) are thus introduced over 8 hours while maintaining the reaction mixture at 120–130° C.

The amount of distillate collected while the two reactants are being run in simultaneously is 46 g. It is 98% n-butyl chloride in composition (determined by GC analysis).

We claim:

1. Process for the preparation of chlorides of substituted or unsubstituted, saturated or unsaturated, aliphatic or cycloaliphatic hydrocarbons by reaction of the corresponding mono- or polyalcohol with phosgene or thionyl chloride, characterized in that the reaction is carried out in the presence of at least one catalyst chosen from the group consisting of (1) hexasubstituted guanidinium halides and their hydrohalides of formula (II):

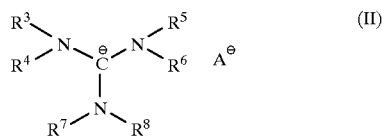

in which the $R^3$ to $R^8$ radicals, which are identical or different, represent substituted or unsubstituted, linear or branched, $C_1$ to $C_{12}$ alkyl groups and/or substituted or unsubstituted, $C_5$ to $C_6$ cycloaliphatic groups and A represents a chlorine or bromine atom or an $HCl_2$ or $HBr_2$ group, and (2) hexasubstituted guanidinium halides and their hydrohalides, grafted via one of their radicals to a silica-based support, of formula (III):

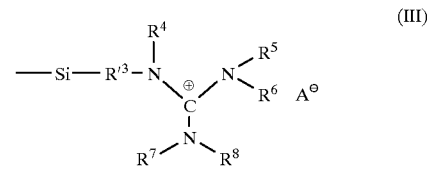

in which $R^4$ to $R^8$ and A radicals have the above meanings and $R'^3$ represents a $C_2$ to $C_{10}$ alkylene group.

2. Preparation process according to claim 1, characterized in that the alcohol is represented by the formula (I):

in which $R^1$ and $R^2$, which are identical or different, represent a hydrogen atom, a saturated or unsaturated, substituted or unsubstituted, linear or branched, $C_1$ to $C_{30}$ aliphatic group, a saturated or unsaturated, substituted or unsubstituted, $C_3$ to $C_{12}$ cycloaliphatic group, a saturated or unsaturated, substituted or unsubstituted, $C_1$ to $C_{30}$ alkoxy group, or a substituted or unsubstituted aryl or aryloxy group; or else in which $R^1$ and $R^2$ together form, with the carbon atom which they are attached, a saturated or unsaturated, substituted or unsubstituted, $C_3$ to $C_{12}$ cycloaliphatic group.

3. Process according to claim 2, characterized in that the substituents of the $R^1$ and $R^2$ radicals are chosen from halogen atoms, hydroxyl groups, saturated or unsaturated, substituted or unsubstituted aliphatic groups, haloaliphatic groups, saturated or unsaturated, substituted or unsubstituted cycloaliphatic groups, substituted or unsubstituted aryl groups, saturated or unsaturated, substituted or unsubstituted araliphatic groups, alkoxy groups, polyalkoxy groups, alkoxyaryl groups, aryloxy groups, nitro groups and cyano groups.

4. Process according to claim 1, characterized in that A represents chlorine or the $HCl_2$ group.

5. Process according to claim 1, characterized in that the $R^3$ to $R^8$ radicals, which are identical or different represent $C_1$ to $C_4$ alkyl groups and the $R'^3$ radical represents the $—(CH_2)_3—$ group.

6. Process according to claim 1, characterized in that the amount of catalyst used is between approximately 0.001 and approximately 0.20 mol of guanidinium group per mole of hydroxyl group to be converted.

7. Process according to claim 1, characterized in that the amount of phosgene is between approximately 1 and approximately 10 mol per mole of hydroxyl group to be converted.

8. Process according to claim 1, characterized in that the temperature is between approximately 20° and approximately 150° C.

9. Process according to claim 1, characterized in that the reaction is carried out in a solvent medium which is inert with respect to compounds and with a boiling point greater than the reaction temperature.

10. Process according to claim 1, characterized in that the process is carried out continuously.

11. Process according to claim 10, characterized in that the alcohol is propargyl alcohol.

12. Process according to claim 11, characterized in that the reaction temperature is between approximately 90° and approximately 130° C.

* * * * *